US012066415B2

(12) United States Patent
Kameoka et al.

(10) Patent No.: US 12,066,415 B2
(45) Date of Patent: Aug. 20, 2024

(54) LOW COST AND WIRELESS GAS SENSING PAPER SENSOR HAVING UHF RANGE

(71) Applicant: The Texas A&M University System, College Station, TX (US)

(72) Inventors: Jun Kameoka, College Station, TX (US); Onder Dincel, College Station, TX (US); Ting-Yen Chi, College Station, TX (US)

(73) Assignee: The Texas A&M University System, College Station, TX (US)

( * ) Notice: Subject to any disclaimer, the term of this patent is extended or adjusted under 35 U.S.C. 154(b) by 348 days.

(21) Appl. No.: 17/554,138

(22) Filed: Dec. 17, 2021

(65) Prior Publication Data

US 2022/0196619 A1    Jun. 23, 2022

Related U.S. Application Data

(60) Provisional application No. 63/127,391, filed on Dec. 18, 2020.

(51) Int. Cl.
| | |
|---|---|
| *G01N 31/00* | (2006.01) |
| *G01N 31/22* | (2006.01) |
| *G08C 17/02* | (2006.01) |
| *G01N 33/00* | (2006.01) |
| *G01N 33/02* | (2006.01) |

(52) U.S. Cl.
CPC ........... *G01N 31/223* (2013.01); *G08C 17/02* (2013.01); *G01N 33/0047* (2013.01); *G01N 33/0054* (2013.01); *G01N 33/02* (2013.01)

(58) Field of Classification Search
None
See application file for complete search history.

(56) References Cited

U.S. PATENT DOCUMENTS

| | | | | |
|---|---|---|---|---|
| 7,730,772 | B2 * | 6/2010 | Cook | ................. B60C 23/0449 |
| | | | | 73/717 |
| 7,777,623 | B2 * | 8/2010 | Albsmeier | ............. G01D 21/00 |
| | | | | 340/870.01 |
| 9,689,828 | B2 * | 6/2017 | Bridges | .................. G01D 3/032 |
| 10,395,162 | B1 * | 8/2019 | Vougioukas | ..... G06K 19/07773 |

* cited by examiner

*Primary Examiner* — Brandi N Hopkins
*Assistant Examiner* — Nigel H Plumb
(74) *Attorney, Agent, or Firm* — Schwegman Lundberg & Woessner, P.A.

(57) ABSTRACT

A system for providing an indication of the presence of molecular structures in a medium is provided. The system includes a radio frequency (RF) wireless antenna, battery-less sensor, and a network analyzer. The sensor has an ultra-high frequency dipole antenna that transmits data to the RF wireless antenna and a sensing element. The sensing element is operatively coupled to the dipolar antenna and detects the presence of molecular structures. When molecular structures are detected, data indicative of the presence of the molecular structures is transmitted to a radio frequency (RF) wireless communication antenna from the dipole antenna. The network analyzer receives the data from the RF wireless antenna and analyzes the data to determine a concentration of molecular structures.

20 Claims, 11 Drawing Sheets

LOW COST AND WIRELESS GAS SENSING PAPER SENSOR HAVING UHF RANGE

PRIORITY

This application claims the benefit of priority to U.S. Provisional Application Ser. No. 63/127,391, filed Dec. 18, 2020, which is incorporated by reference herein in its entirety.

TECHNICAL HELD

The present disclosure generally relates to sensors. More specifically, various embodiments relate to systems that incorporate paper based sensors in a controlled environment.

BACKGROUND

When a merchant is selling a product that has a finite shelf life, the merchant typically relies on a date stamp to determine when the product has exceeded the shelf life. To further illustrate, food products, such as meat products or diary products, typically have a sell-by date stamped thereon. Once the sell-by date has been exceeded, the presumption is that the food product is no longer safe to consume. However, these sell-by dates may not accurately reflect when the food product is no longer safe for consumption. Often times, food manufacturers and retailers determine these dates based on various factors, such as the characteristics of the food product, the packaging, and the temperature at which the product will be stored. Due to the inexact nature of determining sell-by dates, the possibility exists that the product will not actually be unfit for consumption at the expiration of the sell-by date. In other words, the merchant may prematurely dispose the product. Even worse, due to unforeseen circumstances, the product may no longer be safe for consumption prior to the expiration of the sell-by date.

In a different scenario, during the treatment of patients, tests may need to be run to determine a diagnosis of a patient. For example, when testing for C-reactive protein levels in a patient, blood must be drawn from the patient and submitted for testing. Similarly, when testing for other components in blood that can be indicative of various medical conditions, such as testing for Methylmalonic acid levels in a patient, again, blood must be drawn from the patient and submitted for testing.

Accordingly, what is needed is system that can test for the presence of various particulates in an air sample. Moreover, the system should be able to wirelessly transmit data gathered from the air sample to a remotely located device for analysis at the remotely located device.

SUMMARY

Examples relate to a wireless, battery less sensor that can be used to detect various conditions of an area within which the sensor is located. The sensor can include a dipole antenna that is electrically coupled with a sensing element. The sensing element can include either a molecular imprinted conductive (MIP) element or a non-conductive polymer sensing element. When the sensor is in the area, in an example, the MNP captures molecular structures that are in the atmosphere. In some examples, a user can provide a sample, such as breathing on the MIP, where molecular structures in the breath of the user are captured by the MIP. The sensing element can be configured to detect molecular structures captured by the MIP. In an example, the sensor can be part of a system that is configured to monitor the area and provide an analysis of the area. In addition to the sensor, the system can include a radio frequency (RF) wireless antenna that can communicate with the dipole antenna of the sensor. During a sensing operation, the dipole antenna can be energized based on a RF signal received from the RF wireless antenna. In an example, energization of the dipole antenna causes a signal to be passed through the MIP. The impendence caused by the molecular structures can be measured and provided as data to the network analyzer. In particular, the RF wireless antenna can communicate with a network analyzer and provide the data gathered from the MIP to the network analyzer. In an example, the network analyzer can then determine the presence of the molecular structures captured and detected by the MIP and an amount of the molecular structures captured by the MIP.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate possible and alternative examples of how the disclosure can be made and used and are not to be construed as limiting the disclosure to only the illustrated and described examples, Further features and advantages will become apparent from the following, more detailed, description of the various aspects, embodiments, and configurations of the disclosure, as illustrated by the drawings referenced below.

DETAILED DESCRIPTION

Examples relate to a wireless, battery less sensor that can be used to detect various conditions of an area within which the sensor is located. The sensor can include a dipole antenna that is electrically coupled with a sensing element. The sensing element can include either a molecular imprinted conductive (MIP) element or a non-conductive polymer sensing element. When the sensor is in the area, in an example, the MIP captures molecular structures that are in the atmosphere. In some examples, a user can provide a sample, such as breathing on the MIP, where molecular structures in the breath of the user are captured by the MIP.

"Molecular structures," as the term is used generally herein, can include but are not limited to organic and inorganic chemical compounds, organic and inorganic particles, and the like. Organic chemical compounds can include alcohols (for example, alcohols such as ethanol, methanol, butanediol, 3-methylbutan-1-ol, 2-methylpropan-1-ol, 3-hydroxybutan 2-one, and butan-2,3-dione) carboxylic acids (for example, butanoic and hexanoic acids), ketones (for example, acetone), aldehydes (for example, acetaldehyde, hexanal, and malondialdehyde), and hydrocarbons (for example, pentane, isoprene, ethane, 7-ethyl-1,3,5-cycloheptatriene, and aromatic hydrocarbons, such as benzene and derivatives thereof and toluene), and combinations thereof. Inorganic chemical compounds can include nitric oxide (NO), carbon monoxide (CO), and carbon disulfide ($CS_2$). Molecular structures also include but are not limited to substances that are substantially non-volatile, such as fungi, bacteria, isoprostanes, peroxynitrite, or cytokines, which can be present in air condensates or in aerosol particles. Such molecular structures can be indicative of the spoilage of, among other things, milk and meat.

The sensing element can be configured to detect molecular structures captured by the MIP. In an example, the sensor can be part of a system that is configured to monitor the area and provide an analysis of the area. In addition to the sensor, the system can include a radio frequency (RF) wireless antenna that can communicate with the dipole antenna of the sensor. During a sensing operation, the dipole antenna can be energized based on a RF signal received from the RF wireless antenna. In an example, energization of the dipole antenna causes a signal to be passed through the MIP. The impendence caused by the molecular structures can be measured and provided as data to the network analyzer. In particular, the RF wireless antenna can communicate with a network analyzer and provide the data gathered from the MIP to the network analyzer. In an example, the network analyzer can then determine the presence of the molecular structures captured and detected by the MIP and an amount of the molecular structures captured by the MIP.

Figure 1:
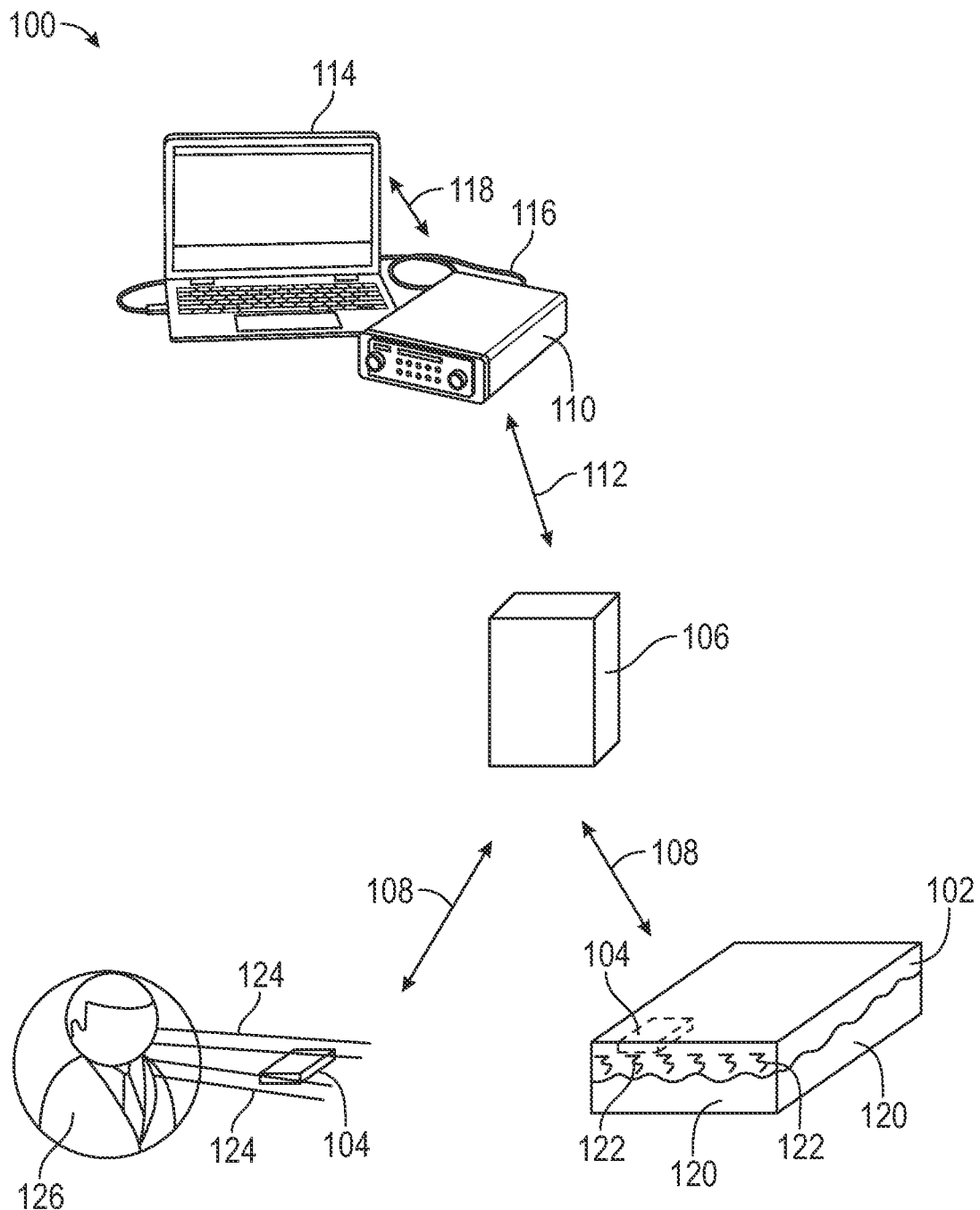
FIG. 1 illustrates an environment which includes a system for monitoring molecular structures in an area, in accordance with an example of the present disclosure.

Now making reference to the Figures, and more specifically to FIG. 1, an environment 100 is shown which includes a system for monitoring molecular structures in an area 102, in accordance with an example of the present disclosure. The system can include a MIP sensor 104 that wirelessly communicates with a RF wireless antenna 106, as shown with wireless signals 108. In an example, the RF wireless antenna 106 can be a dipole antenna. Moreover, the RF wireless antenna 106 can be UWB antenna. The system can also include a network analyzer 110 that wirelessly communicates with the RF wireless antenna 106, as shown with wireless signal 112. Moreover, the system can include a computing device 114 having either a wired connection 116 or a wireless connection 118 with the RF wireless antenna 106.

The area 102 can correlate to a food package, such as a meat package, an egg carton, a dairy carton, or the like. In further examples, the area 102 can correlate to a room where the MIP sensor 104 detects molecular structures in the room. In an example, the MIP sensor 104 is located inside the area 102. Thus, if the area 102 is a meat package, an egg carton, or a dairy carton, the MIP sensor 104 can be located inside of the package and proximate to the contents, such as contents 120. In an example, the contents 102 can correspond to a food product, such as meat, eggs, or any type of dairy product.

As will be discussed further on, the MIP sensor 104 can detect emissions 122 from the contents 120 within the area 102. The MIP sensor 104 can be physically separate from the RF wireless antenna 106. In an example, the RF wireless antenna 106 can be any distance away from the MIP sensor 104. In an example, the RF wireless antenna 106 can be up to 30 cm away from the MIP sensor 104. In an example, the RF wireless antenna 106 can be a circularly polarized RFID antenna.

As noted above, the MIP sensor 104 can be configured to detect and/or capture molecular structures in the area 102. Now making reference to FIG. 2, an example of the MIP sensor 104 in FIG. 1 is shown, in accordance with an example of the present disclosure. In an example, the MIP sensor 104 can be a low cost and synthetic paper sensor that can detect specific volatile organic compounds, which can include the aforementioned molecular structures, The MIP sensor 104 can be configured to detect the presence of any compound, either organic or inorganic, such as ammonia ($NH_3$), from the area 102. As noted above, contents 120 can be a food product. In further examples, the contents 102 can be the human body or a portion of the human body, any portion of a plant, such as a plant leaf, or any type of medical diagnostics. Furthermore, the MIP sensor 104 can detect the presence of bio emanates or biological compounds. In an example, the MIP sensors 104 can detect the presence of any compounds by capturing the compounds.

In an example, the MIP sensor 104 can include a dipole antenna 200 that flanks a MIP conductive polymer sensing element 202 of the MIP sensor 104. The dipole antenna 200 can receive power from and transmit data to the RF wireless antenna 106 using ultra-high frequency (UHF) communications in a range between about 0.75 GHz to about 1.5 GHz. UHF has a longer a communication range and can penetrate through a plastic wall associated with the area 102 for sensing a signal, thus allowing placement of the MIP sensor 104 inside of the area 102, as shown with reference to FIG. 1. By using UHF, the MIP conductive polymer sensing element 202 can have molecular structures 314 (FIG. 3) that can hybridize with specific VOC molecules including alcohols, ketones, aldehydes, organic acids, volatile fatty acids, ethyl esters, sulfur, and nitrogen. In an example, the dipole antenna 200, which can be chipless, can be integrated with the MIP conductive polymer sensing element 202, which can function as a UHF-RFID tag, In an example, the MIP sensor 104 can operate without a chip for various sensing applications. Moreover, the MIP sensor 104 can be formed from synthetic paper and fabricated using an inkjet printing protocol developed with a Fujifilm™ Dimatix™ Materials Printer 2830 available from Fujifilm™ headquartered in Tokyo, Japan. In an example, Novacentrix™ JS series conductive ink available from Novacentrix™ located in Austin, TX, can be used during inkjet printing. In an example, the operation parameters for an inkjet printer that can be used to form the MIP sensor 104 are shown below with reference to Table 1:

| Parameter | Nozzle Spacing | Nozzles Activated | Nozzle Diameter | Frequency | Cartridge Size |
|---|---|---|---|---|---|
| Value | 254 μm | 16 | 21 μm | 30 kHz | 10 pL |
| Parameter | Substrate Temp | Jetting Frequency | Applied Voltage | DropSpacing | Drop Angle |
| Value | 30° C. | 5 Hz | 30 V | 20 μm | 4.4° |

Furthermore, the MIP sensor 104 can be printed with an offset printer for mass production. In particular, the MIP sensor 104 can be made on an inkjet printer and can include the MIP conductive polymer sensing element 202 configured to sense for $NH_3$. The MIP conductive polymer sensing element 202 can be made with a conductive polyaniline (PANI) electrode, which can be a PANI conductive polymer and will be discussed further below. Moreover, the MIP conductive polymer sensing element 2020 can be made with poly(3,4-ethylenedioxythiophene) polystyrene sulfonate (PEDOT PSS.).

MIP technology can be used to create a binding site for biological or chemical material on a PANI electrode formed by the MIP conductive polymer sensing element 202. In an example, the biological or chemical material can be used to bind components in an environment being tested with the MIP sensor 104, which can include the biological or chemical material. The binding of the biological material on a MIP surface of the MIP sensor 104 can change the electrical properties of the MIP conductive polymer sensing element 202 and the sample by changing a charge carrier density.

Figure 3:
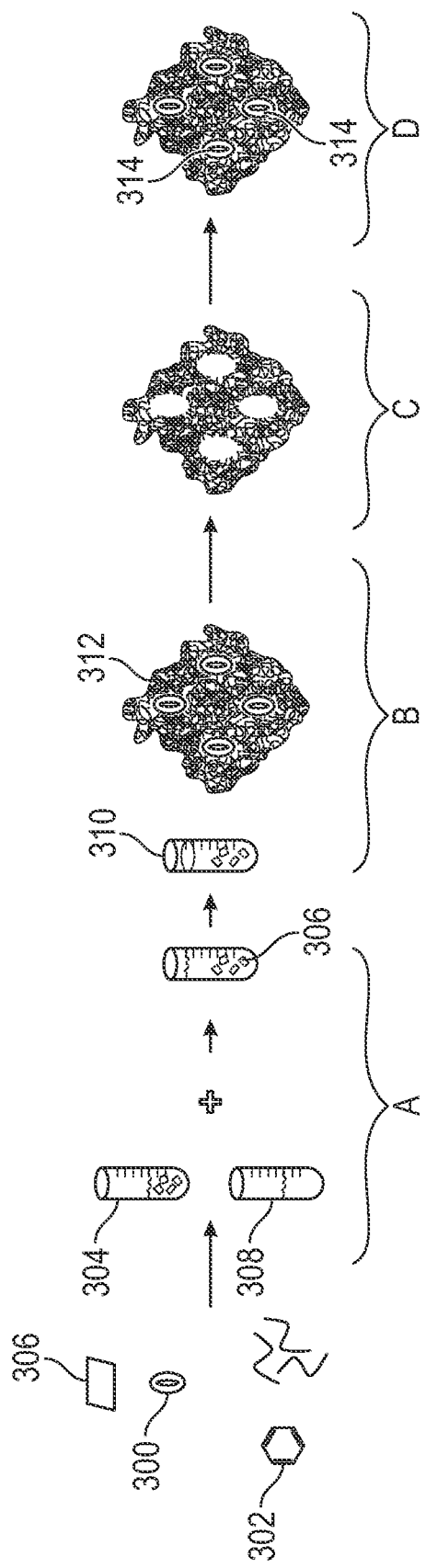
FIG. 3 illustrates a method of fabricating an electrode for the MIP sensor of FIG. 1 that can be used to monitor biological or chemical components, in accordance with an embodiment of the present disclosure.
Figure 4:
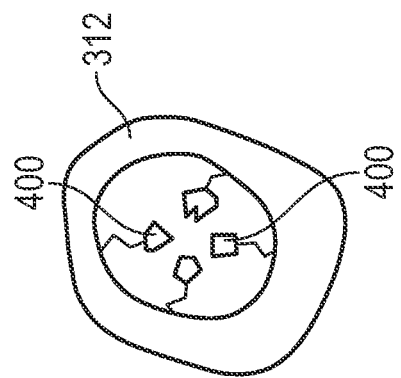
FIG. 4 shows testing components molecularly imprinted within a PANI electrode formed using the method of FIG. 3, in accordance with an embodiment of the present disclosure.

An example of forming the MIP conductive polymer sensing element 202 is shown with reference to FIGS. 3 and 4. Now making reference to FIG. 3, a method of fabricating an electrode for the MIP sensor 104 that can be used to monitor biological or chemical components is shown. Initially, a test sample 300 and a monomer 302 are combined. In an example, the test sample 300 can be any biological or chemical component, such as any type of bacteria or virus, nitrogen, phosphate, carbon, or the like. Furthermore, the test sample 300 can include other biological organisms such as biomolecules, and biomarkers such as protein. The test sample 300 can include an organic or inorganic compound, a bio emanate, and other biological compound. As such, when a sensor, such as the MIP sensor 104, is formed with the test sample 300, the MIP sensors can detect one of organic and inorganic compounds, bio emanates, and biological compounds. In addition, the monomer 302 can be any type of precursor, such as hydrogel, a polymer, a conductive ink, or the like. As shown at an operation (A) in FIG. 3, the test sample 300 and the monomer 302 are combined to form a test sample/monomer solution 304. Afterwards, a substrate 306 is dipped into the test sample/monomer solution 304. At an operation (B), the test sample/monomer solution 304 is combined with an oxidant 308 to form a PANI solution 310. In accordance with an example, the substrate 306 can remain in the test sample/monomer solution 304 as the test sample/monomer solution 304 is combined with the oxidant 308 to form the PANI solution 310. Alternatively, the PANI solution 310 can be first formed and then the substrate 306 can be dipped into the PANI solution 310.

In the operation (B) and in an operation (C), portions of the test sample 300 are removed to form PANI electrodes 312 within the substrate 306 After removal of the portions of the test sample 300, portions of the test sample 300 can remain within the PANI electrodes 312 such that testing components 400 are molecularly imprinted within the PANI electrode 312, as more clearly shown with reference to FIG. 4. In an example, operation (C) can result in a MIP structure, such as the MIP conductive polymer sensing element 202.

Figure 2:
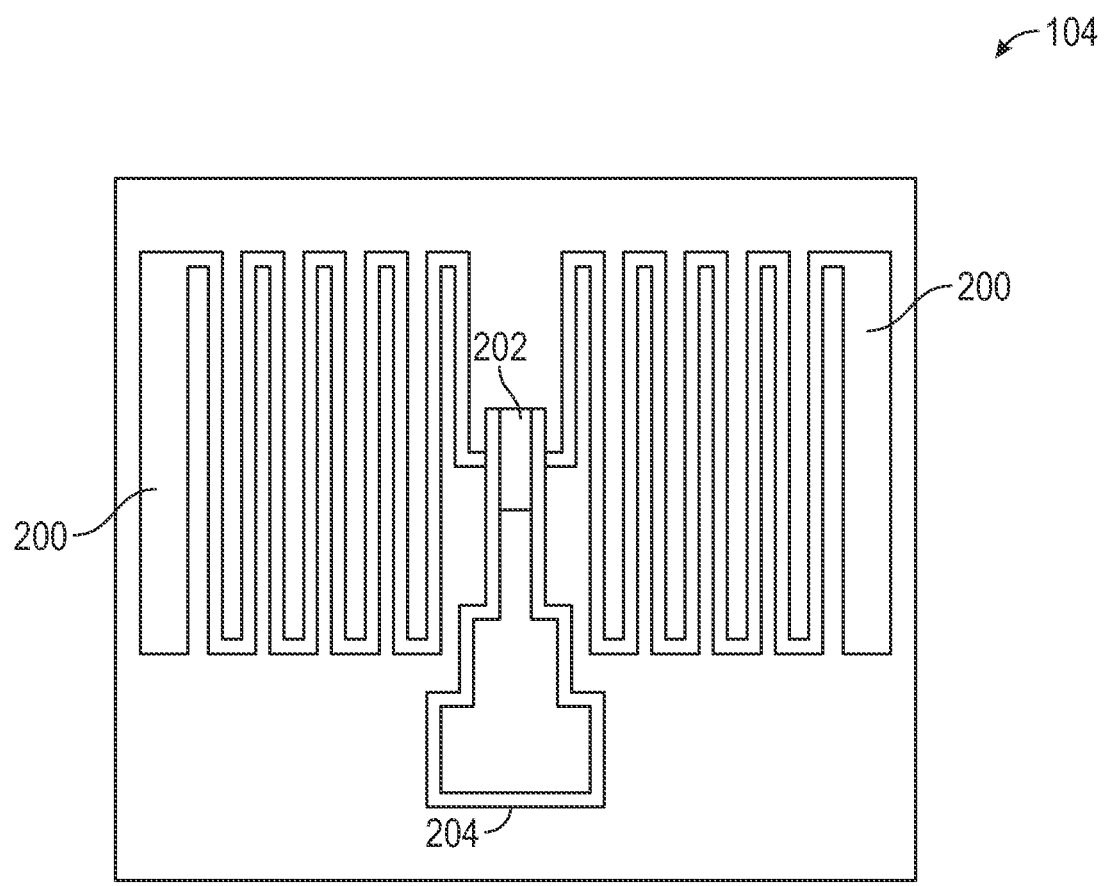
FIG. 2 shows an example of a MIP sensor in FIG. 1, in accordance with an example of the present disclosure.

As discussed above, when the MIP conductive polymer sensing element 202 with reference to FIGS. 2-4 is used to monitor a desired parameter, the MIP conductive polymer sensing element 202 can capture components being monitored by the MIP sensor 104. For example, at an operation (D), the MIP conductive polymer sensing element 202 can capture the molecular structures 314 via the testing components 400. In an example, the operation (D) can be the recognition of testing components upon exposure to targets. The MIP conductive polymer sensing element 202 can be activated and powered up when the MIP conductive polymer sensing element 202 receives RF communications, as discussed above. Upon activation via any device capable of RF communications, the MIP conductive polymer sensing element 202 monitors and can then be used to determine an amount of components within the PANI electrode 312 via the network analyzer 110. In accordance with these examples, resistance levels measured by the PANI electrodes 312 change based on concentrations in a test sample. For example, when the MIP conductive polymer sensing element 202 captures the molecular structures 314, these components, which may correspond to molecules, change the resistance of the PANI electrode 312. To further illustrate, when a pulse signal is received and injected into the PANI electrode 312, the molecular structures 314 can either increase or decrease resistance, based on the type of component and the amount. In accordance with another example, the MIP conductive polymer sensing element 202 can include a further electrode, which may be used to calculate the resistance based on the molecular components 314.

In accordance with embodiments of the present disclosure, the higher the concentration of the molecular structures 314 within the PANI electrode 312, the higher the impendence and the higher the resistance. Any type of chemical or biological component may be tested with the MIP conductive polymer sensing element 202. For example, in an embodiment where airborne viruses or bacteria are being tested the virus or bacteria can he implanted in the substrate 306 as discussed above with regards to FIGS. 3 and 4 where the airborne viruses and bacteria can correspond to the testing elements 400.

Returning attention to FIG. 2, during operation, the RF wireless antenna 106 can send a RF signal to the MIP sensor 104 via the wireless signal 108, thereby energizing the dipole antennas 200. When the dipole antennas 200 are energized, a current can be caused to be passed through the MIP conductive polymer sensing element 202. In an example, reflection data, such as impedance, can be determined where the impedance is function of resistance and capacitance. In particular, the difference between the signal that is received by the dipole antenna from the RF wireless antenna 106 and the signal that is transmitted by the dipole antenna 200 to the RF wireless antenna 106 can be a measure of the impedance across the MIP conductive polymer sensing element 202. In an example, the impedance can be a function of the resistance from the molecular structures 314 captured by the MIP conductive polymer sensing element 202, a capacitance associated with the MIP conductive polymer sensing element 202, and a reactive component provided by a coil 204 of the MIP sensor 104. In an example, the concentration of the molecular structures 314 in the MIP conductive polymer sensing element 202 can be a function of the impedance measured across the MIP conductive polymer sensing element 202.

In some examples, the impedance can correlate to reflection caused by the molecular structures 314 captured within the MIP conductive polymer sensing element 202. In some examples, reflectance from the molecular structures 314 can be used to directly calculate impedance. For example, if the molecular structures 314 correspond to ammonia ($NH_3$), the reflectance from the $NH_3$ captured in the MIP conductive polymer sensing element 202 can directly correlate to the impedance.

In an example, molecular structures captured by the MIP conductive polymer sensing element 202 can increase a resistance across the MIP conductive polymer sensing element 202. The increased resistance affects the conductance across the MIP conductive polymer sensing element 202 such that the greater the amount of molecular structures captured by the MIP conductive polymer sensing element 202, the lower the conductance across the MIP conductive polymer sensing element 202. In particular, molecular structures hybridize with the MIP conductive polymer sensing element 202. The hybridization of the molecular structures into the MIP conductive polymer sensing element 202 fluctuates the polaron motion due to the local charge modulation that contributes to the change of carrier mobility. The increase or decrease influences the conductivity of the polymer, which enables measurement of the presence of a target analyte. Additionally, the capacitive detection can be also achieved based on an interdigital sensing element. This impedance measurement, which can include resistance as mentioned above along with capacitance, is suited for wireless sensing applications. In an example, once the impedance is determined as discussed above, data associated with the detected impedance can be transmitted to the RF wireless antenna 106 by the dipole antenna 200.

Returning attention to FIG. 1, as discussed above, the dipole antenna 200 can be energized by a signal received from the RF wireless antenna 106. Moreover, the dipole antenna 200 can transmit impedance data determined from the MIP conductive polymer sensing element 202 to the RF wireless antenna 106 via the wireless signal 108. In an embodiment, the RF wireless antenna 106 can be any type of antenna capable of transmitting and receiving signals in the RF LAMB range.

In an example, when the RF wireless antenna 106 receives the impedance data from the dipole antenna 200, the RF wireless antenna 106 can transmit the impedance data to the network analyzer 110 as shown by the wireless signal 112. In an example, the network analyzer 110 can be a vector network analyzer that can measure transmitted and reflected waves as a signal passes through the MIP conductive polymer sensing element 202. In an example, by measuring the transmitted and reflected signals, the characteristics of MIP conductive polymer sensing element 202 can be determined. For example, a concentration of the molecular structures 314 captured by the MIP conductive polymer sensing element 202 can be determined. In an example, the concentration of the molecular structure captured by the MIP conductive polymer sensing element 202 can correlate to a concentration of the molecular structures 314 within the area 102. Moreover, in an example, the concentration of the molecular structures captured by the MIP conductive polymer sensing element 202 can indicate whether or not a product within the area 102 has become spoiled, e.g., in the case of a food product, if the food product has become unsuitable for consumption. It should be noted that in an example when the MIP conductive polymer sensor element 202 captures the molecular structures 314, the MIP sensor 104 has detected the presence of the molecular structures 314 by virtue of the MIP conductive polymer sensor element 202 capturing the molecular structures 314.

To further illustrate, the contents 120 may release emissions 122 having the molecular structures 314. When the emissions 122 pass over the MIP conductive polymer sensing element 202 of the MIP sensor 104, the molecular structures are captured by the MIP conductive polymer sensing element 202 via the testing elements 400. In the illustration, the emissions 122 can correlate to $NH_3$. When the $NH_3$ is captured within the MIP conductive polymer sensing element 202 of the MIP sensor 104, this data will be transmitted to the network analyzer 110 as impedance data, as discussed above, In an embodiment, the network analyzer can determine a concentration of the molecular structure, such as the based on the impedance, and then send this information either wirelessly via the wireless signal 118, or via a wired connection 116, to the computing device 114 for display. Therefore, by virtue of determining a concentration of $NH_3$ that is emitted by a food sample, the network analyzer 110 can determine an amount of molecular structures 314 emitted by the contents 120. Based on the amount of detected molecular structures, a determination can be made of the contents 120 have spoiled, i.e., the detected amount exceeds a threshold. In an example, the network analyzer 110 can be any type of scalar network analyzer, vector network analyzer, large signal network analyzer, or the like. In an example, the computing device 114 can be a server computer, a client computer, a personal computer (PC), a tablet computer, a laptop computer, a netbook, a set-top box (STB), a personal digital assistant (PDA), a cellular telephone, a smart phone, a mobile device, a wearable device (e.g., a smart watch), or any other type of device capable of displaying information received from the network analyzer 110.

As discussed above, the MIP sensor 104 can be placed within the area 102 and detect molecular structures that are in a gaseous state, such as the emissions 122 when the MIP conductive polymer sensor element 202 captures the molecular structures. In accordance with another example, the MIP sensor 104 can be used to capture emissions 124, such as aerosol emissions, from a user 126, as shown with reference to FIG. 1. In this example, the user may cough, breath, provide a saliva sample, or provide another type of sample including aerosol emissions, on to the MIP sensor 104. Molecular structures within the emission 124 are captured by the MIP conductive polymer sensing element 202. As discussed above, when the MIP sensor 104 is energized by signals received from the RF wireless UWB antenna 106 via the wireless signal 108, the MIP sensor 104 can transmit impedance data to the RF wireless antenna 106 as discussed above. As discussed above, the RF wireless antenna 106 can transmit the impedance data associate with the emissions 124 to the network analyzer for analysis and display on the computing device 114.

Figure 5A:
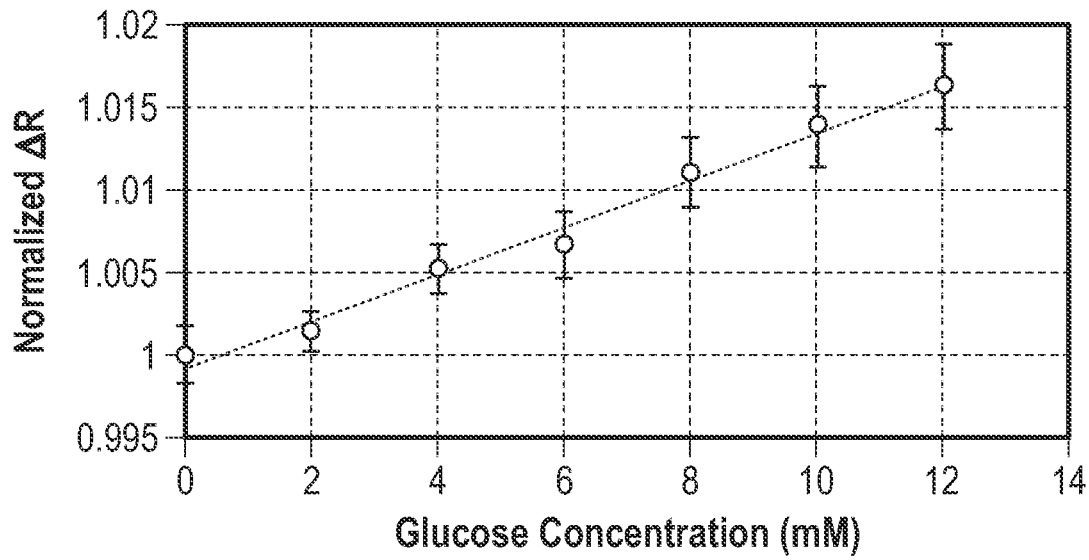
FIGS. 5A-C demonstrate a correlation between components captured by a MIP sensor of FIG. 1 based on a measured resistance, in accordance with an embodiment of the present disclosure.
Figure 5B:
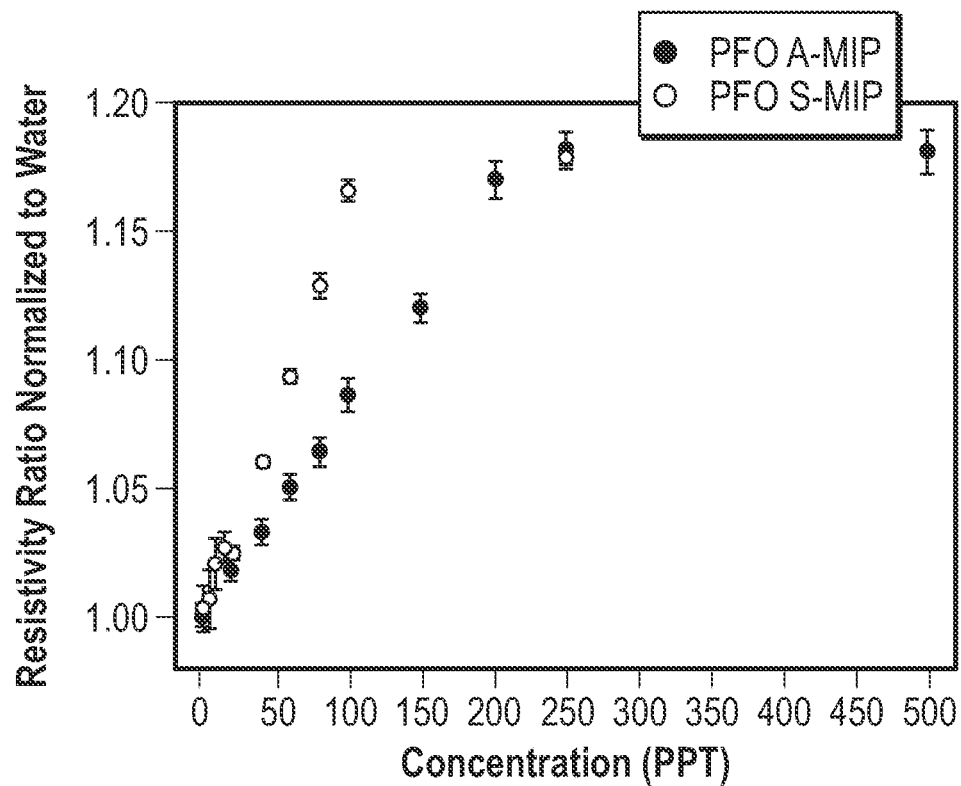
Figure 5C:
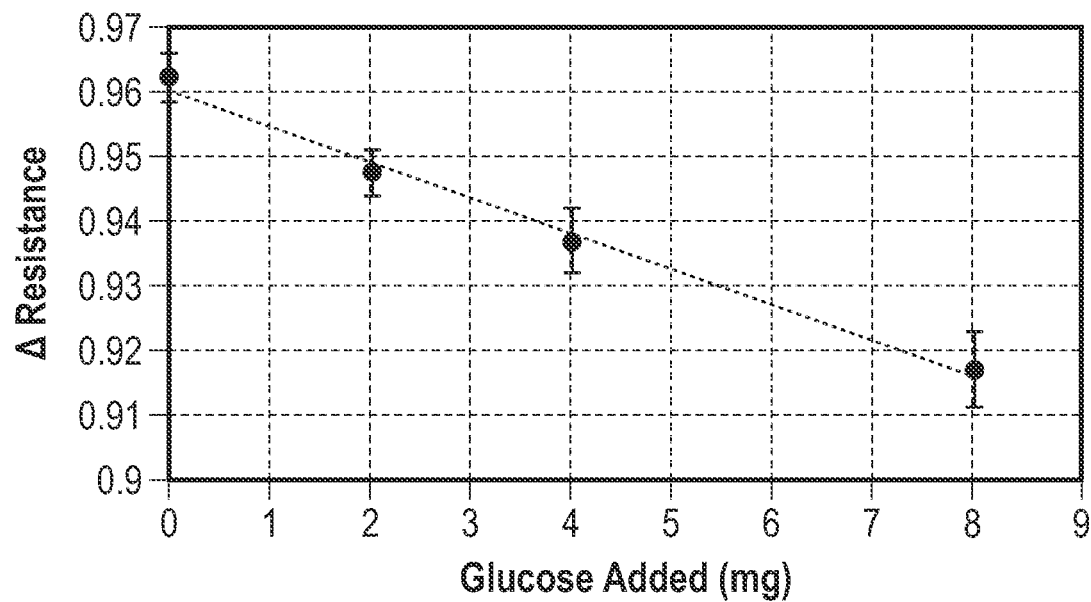

Regarding concentration levels of the molecular structures 314, as may be seen with reference to FIG. 5A, in accordance with embodiments of the present disclosure, the higher the concentration of the molecular structures 314 within the PANI electrode 312, such as glucose, the higher resistance. Additionally, when other testing components, such as perfluorooctanoic acid (PFO-A) or perfluorooctanesulfonic acid (PFO-S) are used, resistance increases as concentration levels of PFO-A or PFO-S increase, as shown with reference to FIG. 5B. Furthermore, in some examples, such as in instances where bovine glucose is being measured, resistance decreases as glucose levels increase, as illustrated with reference to FIG. 5C. The calculated resistance values may be used to determine a concentration value of the molecular structures 314 in the sample being tested. While glucose is described, any type of chemical or biological components may be tested with the MIP sensor 104 as described above. For example, in an embodiment where airborne viruses or bacteria are being tested, instead of glucose, the virus or bacteria may be implanted in the substrate 306 as discussed above with regards to FIGS. 3 and 4. In these examples, the MIP sensor 104 can be used externally, for example in a room, to determine whether or not a virus or bacteria exists in the tested space.

C-Reactive Proteins Example

In some examples, the MIP sensor 104 can be used to detect for C-reactive proteins (CRP). To further illustrate, in the CRP example, the MIP sensor 104 can be formed such that when the user 126 breaths on to the MIP sensor 104 via the emissions 124 in aerosol form, the molecular structures 314 captured by the MIP conductive polymer sensing element 202 from the emissions 124 can be used to test for various cardiovascular diseases. When the MIP sensor 104 is used to detect for CRP, the test sample/monomer solution 304 is formed by mixing 0.2 g of aniline solution with CRP stock solution, then added into 1 M HCl solution to a total volume of 5 mL. In the CRP example, the concentration of the test sample/monomer solution 304 was calculated to be 20 mg/L. The substrates 306 were prepared by cutting polyester paper into strips with the size of 1 cm×0.5 cm. The substrates were immersed into the test sample/monomer solution 304 and soaked for 5 min. In the CRP example, the substrate 306 has moderate hydrophilicity and allows for the uniform formation of the MIP conductive polymer sensing element 202 during polymerization. In the CRP example, the oxidant 308 was prepared by mixing 409 mg of ammonium persulfate with 5 mL of 1 M HCl. The well-mixed oxidant solution was added drop-by-drop into the test sample/monomer solution 304 under stirring to initiate the polymerization of the PANI electrode 312 for the MIP conductive polymer sensing element 202 on the substrate 306. The HCl acted as dopant that enriches the conductivity of the PANI electrode 312 for the MIP conductive polymer sensing element 202 during the reaction. After 10 minutes of polymerization, the substrate 306 was taken out of the solution and washed with deionized water (DI water) multiple times until the eluent was clear and no dark colored PANI particles of the PANI electrode 312 were left in the test sample/monomer solution 304. In the CRP example, in order to remove excess CRP, such as a CRP template, from the PANI electrode 312 for the MIP conductive polymer sensing element 202, the substrate 306 was immersed into an acetic acid solution with a concentration of 0.2% (v/v), followed by sonication for 1 hour. The resulting strips were then rinsed with DI water until the pH reached 7. Afterwards, the strips were air-dried at room temperature (RT, 25° C.) for at least 12 hours. In the CRP example, as a control, non-molecularly imprinted (NIP) PANI paper strips were synthesized following the same protocol described above without the addition of CRP in the monomer solution.

Figure 6:
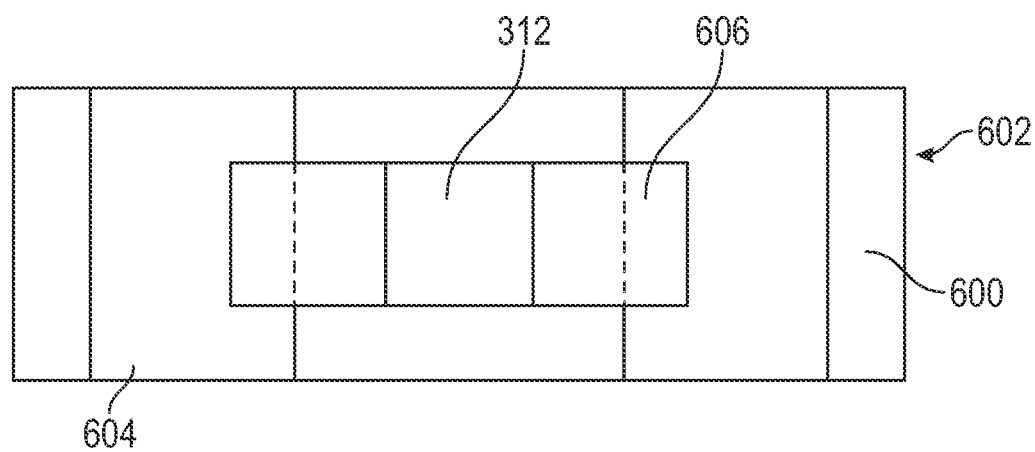
FIG. 6 illustrates a CRP-MIP-PANI paper sensor having functionality similar to the MIP conductive polymer sensing element in FIG. 2, in accordance with an embodiment of the present disclosure.

In the CRP example, after formation of the PANI electrode 312, in order to form the MIP conductive polymer sensing element 202 with the formed PANI electrode 312, the PANI electrode 312 was attached to a piece of stencil 600 with the size of 1 cm×3 cm using a double-sided tape as shown with reference to FIG. 6. Copper tape was cut into pieces 604 with the size of 1 cm×0.635 cm and then placed on both sides of the PANI electrode 312 on the stencil 600 as the electrodes, leaving a 1 mm gap between the PANI electrode 312 and each copper electrode. The PANI electrode 312 and the copper electrodes were physically connected by conductive silver ink 606 to form the MIP conductive polymer sensing element. The whole device was then kept at room temperature for at least 12 hours to allow the silver ink to dry and ensure good conductivity. The control NIP-PANI paper sensors were fabricated following the same procedures above.

In the CRP example, the test sample monomer solution 304 with a series of concentrations of 0, 2, 4, 6, 8 and 10 mg/L were prepared by diluting the stock solution in DI water. 10 μL of these sample solutions with different concentrations were dispensed on the surface of the CRP-MIP-PANI paper sensor 602. The direct current resistance (R) of the CRP-MIP-PANI paper sensor 602 was measured before sample dispensing and 1 hour after sample dispensing by a multimeter such as a Fluke 8846A multimeter available from Fluke Inc. located in Everett, WA The resistance change of the CRP-MIP-PANI paper sensor 602 was also recorded for each CRP concentration as a control.

The CRP concentration can be determined by a resistivity (ρ) change of the CRP-MIP-PANI paper sensor 602 before and after exposure to the CRP samples. The ρ of the paper sensor is related to R and can be described by the following equation (1):

$$\rho = R \cdot \frac{A}{l} \qquad (1)$$

where A is the cross-sectional area and l is the length of the PANI paper strip between the electrodes. Since A and l remain the same for each paper sensor before and after sample dispensing, where is conductivity in Siemens and is positively proportional to the ρ of the paper sensor. As a result, the resistivity change of the paper sensor is positively related to the resistance change of the paper sensor. The resistivity change ratio (Δρ) before and after the sample exposure is normalized based on the CRP concentration at 0 mg/L by the following equation (2):

$$\Delta \rho = \left( \frac{\rho_{after,sample}}{\rho_{before,sample}} \right) \Big/ \left( \frac{\rho_{after,DI\ water}}{\rho_{before,DI\ water}} \right) \qquad (2)$$

In the CRP example, the limit of detection (LoD) of the CRP-MIP-PANI paper sensor was also evaluated. A limit of blank (LoB) can be determined by the equation (3), $$\text{LoB} = \mu_b + \sigma_b \qquad (3)$$

where $\mu_b$ and $\sigma_b$ are the mean value and the standard deviation of blank samples, respectively. Then, the LoD was calculated by the equation (4), $$LoD = LoB + \sigma_s \qquad (4)$$

where $\sigma_s$ is the standard deviation of the sample with a low concentration. By plugging in the mean value and standard deviation from the calibration curve into equations (3) and (4), the LoD of the CRP-MIP-PANI paper sensor 312 were estimated.

Figure 7:
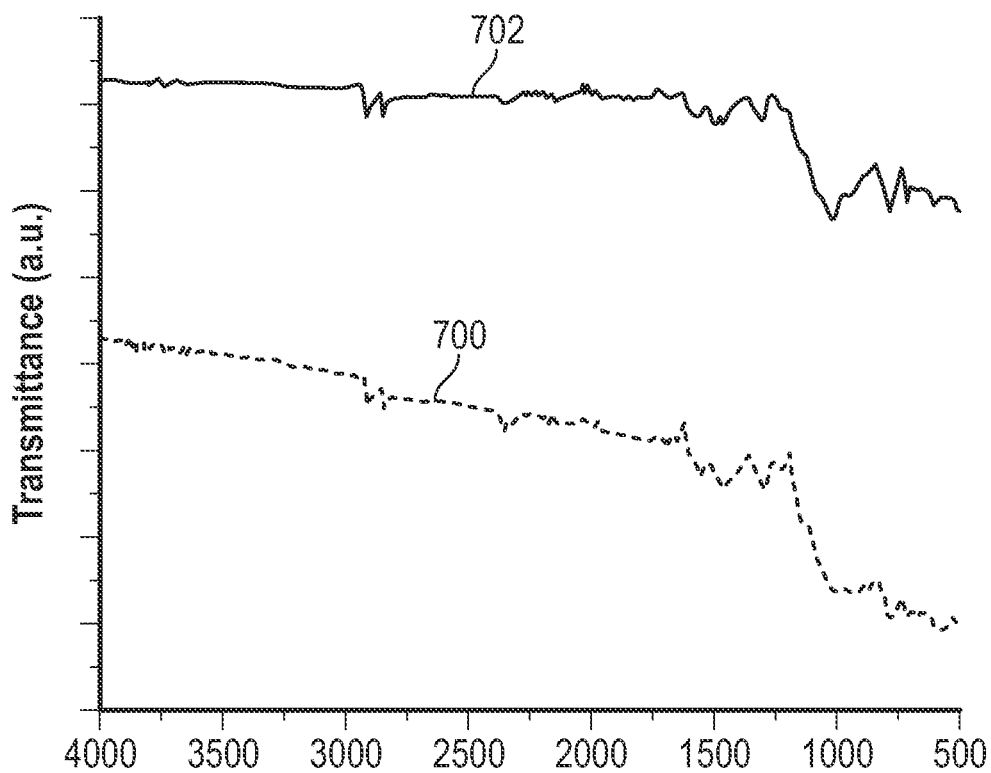
FIG. 7 illustrates a characterization of a sensing area of CRP-MIP-PANI paper sensor, in accordance with an embodiment of the present disclosure.

FIG. 7 illustrates a characterization of a sensing area of the CRP-MIP-PANI paper sensor 312 in the CRP example. The surface of the PFOS-MIP-PANI sensing area was characterized by Fourier-transform infrared spectroscopy. The spectra of NIP-PANI and CRP-MIP-PANI are shown in FIG. 7. The spectra of both show the main bands at the wavenumber of 1590, 1508 and 1308 cm$^{-1}$, which correspond to the ring-stretching vibrations of the quinoid and bensenoid rings of aniline and nitro aniline, respectively. Moreover, in FIG. 7, 700 represents the spectra of the control NIP-PANI while 702 represents the spectra of the CRP-MIP-PANI paper sensor 312. In the CRP example, the transmission percentages are adjusted to an arbitrary unit in order to compare the characteristic peaks.

Figure 8:
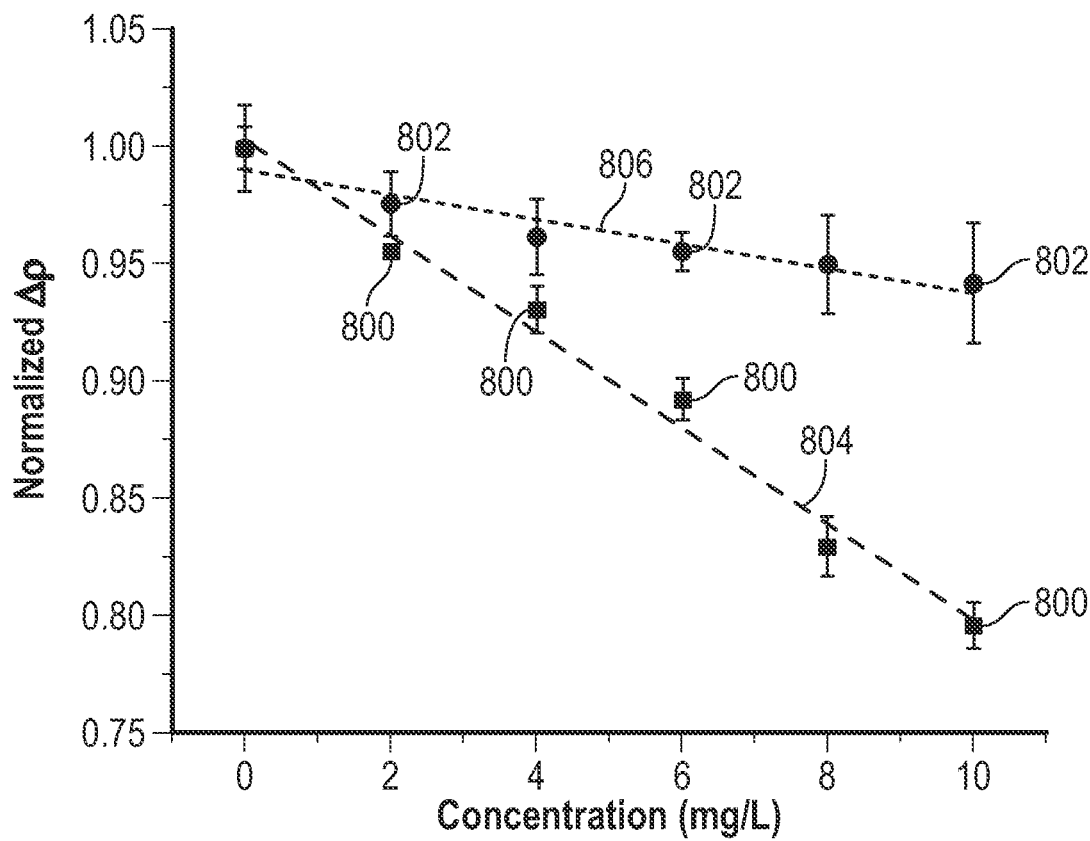
FIG. 8 illustrates a normalized resistivity change ratio zip as a function of the CRP concentration, in accordance with an embodiment of the present disclosure.

FIG. 8 illustrates a normalized $\Delta\rho$ as a function of the CRP concentration. The normalized $\Delta\rho$ of the CRP-MIP-PANI paper sensor 312 shows a negatively linear correlation to the increase of the CRP concentration.

A fitted model of detecting CRP by the CRP-MIP-PANI paper sensor 312 is described by the following linear regression equation (5), $$y = -0.0205x + 1.0034 \qquad (5)$$

with a coefficient of determination ($R^2$) of 0.987. According to equations (3) and (4), the LoD of CRP-NIP-PANI paper sensor 312 was estimated to be 0.390 mg/L.

As shown in FIG. 8, for comparison, a CRP concentration determination was also conducted with the control NIP-PANI paper sensors. Similarly, the fitted model of the NIP-PANI paper sensors is shown in the following equation (6), $$y = 0.0053x + 0.9915 \qquad (6)$$

with the $R^2$ to be 0.918. The LoD in the NIP-PANI paper sensor was estimated to be 7.64 mg/L accordingly.

As may be seen with reference to FIG. 8, results show the CRP-MIP-PANI paper sensor 312 can have a smaller LoD in comparison to the control NIP-PANI sensor. The resistivity ratio of the CRP-MIP-PANI paper sensor 312 can present a larger decrease than that of NIP-PANI paper sensors when exposed to increased CRP concentrations. Thus, the CRP-MIP-PANI sensor 312 can have a higher sensitivity than the MIP-PANI sensor. In particular, FIG. 8 illustrates resistivity ratios 800 and 802 of the CRP-MIP-PANI sensor 312 and a NIP-PANI sensor when the sensors are exposed to various CRP concentrations. Here, the ratios 800 and 802 are respectively fitted to calibration curves 804 and 806 where each point represents the average value of at least three identical measurements.

As noted above with reference to FIG. 1, in some examples, the user can provide aerosol emissions 124 to the MIP sensor 104. In examples where the MIP sensor 104 is configured to test for CRP, based on the aerosol emissions 124, the MIP sensor 104 can be used to determine CRP levels in the user 126 after the user 126 provides the aerosol emissions 124, in accordance with the principles discussed above. Therefore, the MIP sensor 104 can be used for medical diagnostics.

Lentivirus Example

In accordance with examples, a MIP lentivirus sensor that is low cost, that does not require reagent and is able to perform detection in dry environments without bulky equipment is provided. In the lentivirus example, to form the molecular imprinting template for a MIP lentivirus sensor, the lentivirus virus can be blended with a conductive monomer solution that is polymerized on a polyethylene terephthalate (PET) paper substrate. The lentivirus is removed from the molecular imprinted template using a sonication technique and edges of conductive MIP sensing paper can be connected with two copper metal tapes as electrodes to measure the conductance of MIP sensing structures. In the lentivirus example, the conductance of conductive polymer can rely on polaron hopping through $\pi$-$\pi$ bonding. Thus, the absorption of virus on the MIP sensing structure influences the conductance of the MIP sensor. In the lentivirus example, lentivirus can be detected by dispensing solution having the lentivirus to the sensing element within 20 minutes of an attempt to detect lentivirus. The stability of the molecular imprinted structure in air can enable the capture and detection of airborne viruses, thereby preventing a potential outbreak and a large scale lockdown.

In the lentivirus example, in order to synthesize a virus imprinted polyaniline for use with a sensor, 200 μl of aniline, paper strips (1 cm×0.5 cm) for the molecular imprinting template, and 500 μl of the virus stock solution ($2.2\times10^5$ transducing units (TU)/ml) were mixed into 1 M HCl with a final volume of 5 ml as the monomer solution. The oxidant solution was prepared by mixing 409 mg of APS with 5 ml of 1 M HCl in a dropwise manner to initiate polymerization for 10 minutes. In the lentivirus example, the virus concentration in the formed polymer solution was $1.1\times10^4$ TU/ml. The virus templates were removed by ultra-sonicating the strips in acetic acid/methanol solution (v/v=1:6) for 4 hours, followed by rinsing the strips until the pH value of the eluent reached to 7. In an example, v/v relates to a volume ratio. The resulting lentivirus molecularly imprinted PANI (Virus-MIP-PANI) paper strips were air-dried at ambient temperature overnight. The monomer solution without lentiviruses was used to synthesize non-molecularly imprinted control NIP-PANI.

In the lentivirus example, in order to fabricate the Virus-MIP PANI sensor, a NIP-PANI strip and another Virus-MIP-PANI strip were integrated with a plastic stencil (2 cm×2.5 cm) as the substrate and copper tapes (1 cm×¼ in) as the contact electrodes using double-sided tape. The strip and electrode were separated by a 1 mm-gap which was then filled with a silver conductive paste. The silver paste was cured at 25° C. for at least 12 hours to assure the optimal conductivity.

In order to test the efficacy of the Virus-MIP-PANI sensor formed above, 30 μl of virus solution was dispensed on the middle of the PANI strip as the sensing element (0.5 cm×0.5 cm) and saturated for 30 min. Afterwards, the PANI strip was air-dried at 25° C. The resistance of the PANI electrode was measured by a multimeter such as Fluke 8846A multimeter available from Fluke Inc. located in Everett, WA. in a direct current mode after drying for 30 minutes. Resistance can be converted to resistivity as shown in the following Equation 7:

$$\rho=R/AL \quad (7)$$

where A and L are the cross-sectional area and the longitudinal length of the PANI sensing element. In addition, the resistivity of the after virus-exposure was divided by the resistivity before virus-exposure to calculate the resistivity ratio which is the output signal of the sensor. The resistivity ratios were further normalized to the ratios that exposed to phosphate-buffered saline (PBS) by using the following Equation (8):

Normalized resistivity ratio=(virus sample resistivity ratio)/(resistivity ratio of PBS) (8)

To calculate the subtracted resistivity ratios, the normalized resistivity ratios of Virus-MIP-PANI were subtracted by that of NIP-PANI as shown in the following Equation (9):

Subtracted resistivity ratio=(normalized resistivity ratio, Virus-MIP-PANI)−(normalized resistivity ratio, NIP-PANI) (9)

The LoD was estimated by using Equation (10) below, where the slope (m) was obtained by a linear regression model using graphing software, such as in SigmaPlot™ available from Systat™ located in Palo Alto, Ca. σ is the standard errors of blank samples that were exposed to PBS.

LoD=3σ/m (10)

Figure 9:
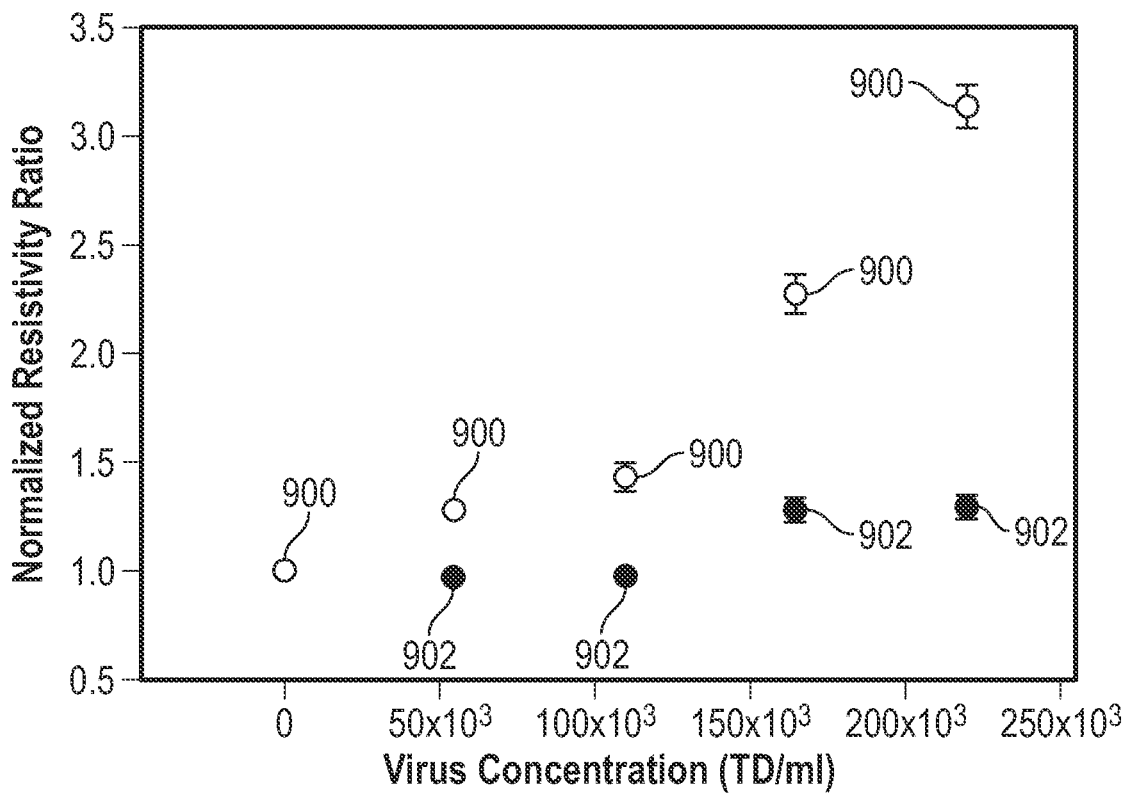
FIGS. 9 and 10 illustrate a comparison between resistivity ratios for a Virus-MIP PANI sensor and a control NIP-PANI sensor, in accordance with an embodiment of the present disclosure.
Figure 10:
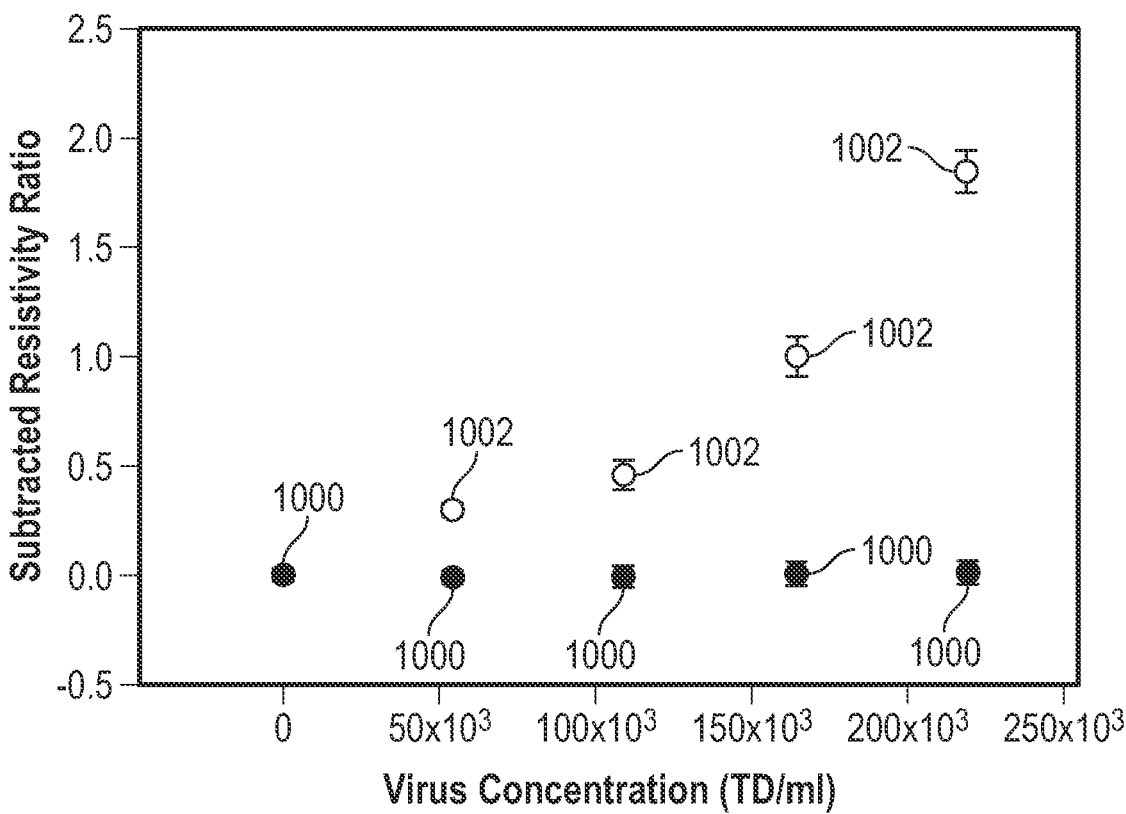

FIG. 9 illustrates a comparison between the resistivity ratios for the Virus-MIP PANI sensor and the NIP-PANI sensor, where the NIP-PANI sensor was a control. In FIG. 9, resistivity ratios are shown for the Virus-MIP PANI sensor and the control NIP-PANI sensor after being exposed to lentiviruses and dried for 30 minutes. As may be seen with reference to FIG. 9, normalized resistivity ratios and the subtracted ones both increased as virus concentrations increased, particularly for ratios 900 of Virus-MIF-PANI, which have a significant difference than those of ratios 902 NIP-PANI. As shown with reference to FIG. 10, when the resistances 1000 by the NIP-PANI are assigned a zero resistance as a baseline, and the resistances associated with the NIP-PANI are subtracted from the resistance ratio 1002 of Virus-MIP PANI, a linear regression equation of the range from 0 to $2.2 \times 10^5$ TU/ml is y=0.0000079574x−0.1546 with a $R^2$ value of 0.914. By using Equation 10, the LoD for lentivirus sensing by the Virus-MIP-PANI electrodes was estimated to be 4217 TD/ml in the lentivirus example.

As noted above with reference to FIG. 1, in some examples, the user can provide aerosol emissions 124 to the MIP sensor 104. In examples where the MIP sensor 104 is configured to test for the lentivirus, based on the aerosol emissions 124, the MIP sensor 104 can be used to determine lentivirus levels in the user 126 after the user 126 provides the aerosol emissions 124, in accordance with the principles discussed above.

Figure 11:
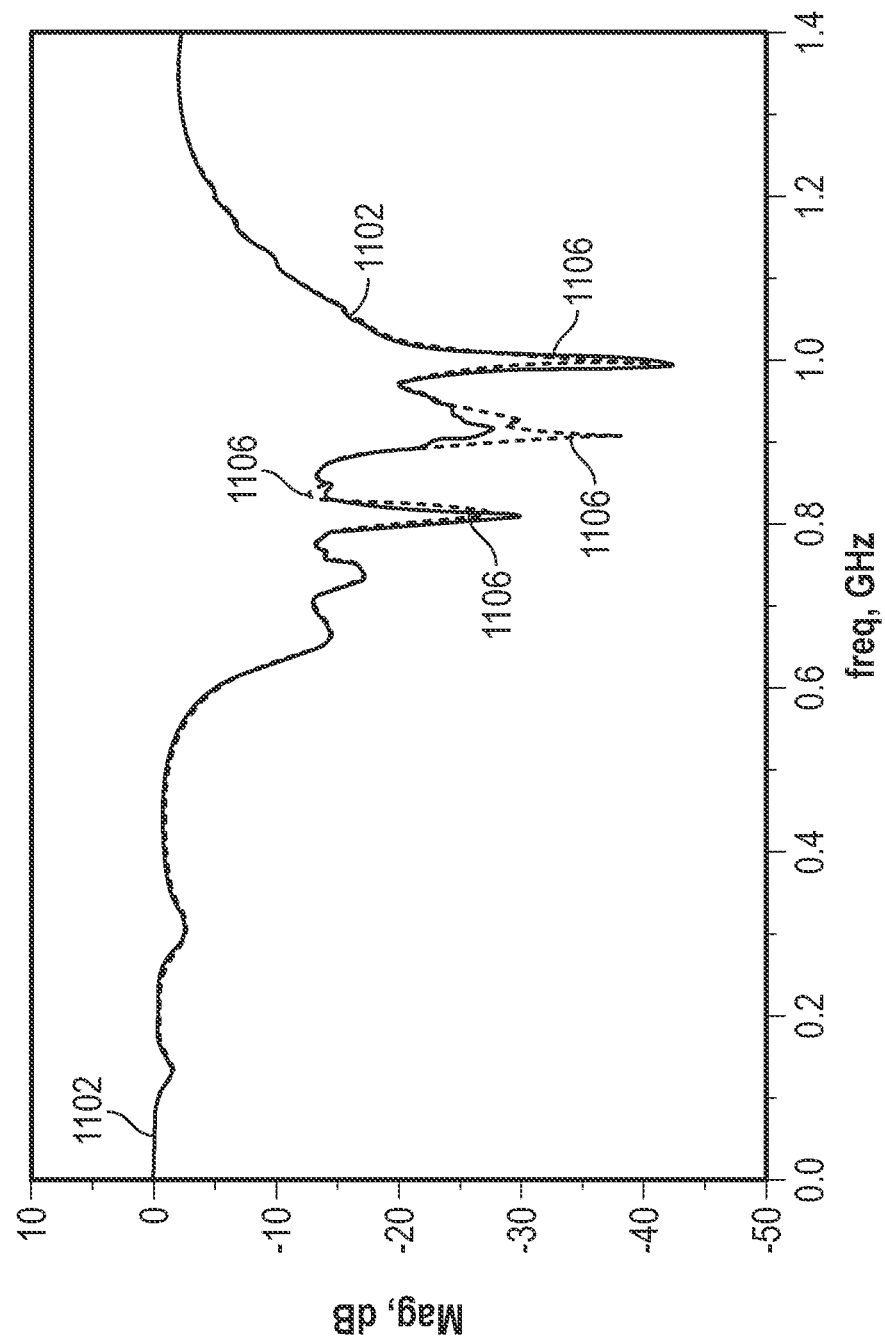
FIG. 11 illustrates a graph for a reflective coefficient as a function of transmitting frequency, in accordance with an embodiment of the present disclosure.

FIG. 11 illustrates a graph for a reflective coefficient as a function of transmitting frequency. A line 1100 in this graph can indicate the reflective coefficient under an atmospheric environment in the area 102. There can be three resonant configurations, 0.8 GHz, 0.9 GHz, and 1.0 GHz. In the example reflected in FIG. 11, 2000 ppm $NH_3$ vapor is injected into the area 102. In this example, the MIP sensor 104 detected the $NH_3$ vapor quickly as shown at line 1102 of the graph. As may be seen, there can be three peak changes in the profiles, including 0.9 GHz. Using this approach, configurations for the MIP sensor 104 can be optimized. Moreover, in an example, the line 1102 can be used to optimize the MIP sensor 104.

In addition to the applications discussed above, examples can be used to detect for Methylmalonic acid (MMA). MMA can be an early indicator of Vitamin B12 deficiencies. Moreover, MMA can be a biomarker for cancer diagnosis. In examples, MMA particles can be introduced into the MIP sensor 104 as the testing elements 400. As noted above with reference to FIG. 1, in some examples, the user can provide aerosol emissions 124 to the MIP sensor 104. In examples where the MIP sensor 104 is configured to test for MMA, based on the aerosol emissions 124, the MIP sensor 104 can be used to determine MMA levels in the user 126 after the user 126 provides the aerosol emissions 124, in accordance with the principles discussed above. Therefore, the MIP sensor 104 can be used for medical diagnostics.

Figure 12:
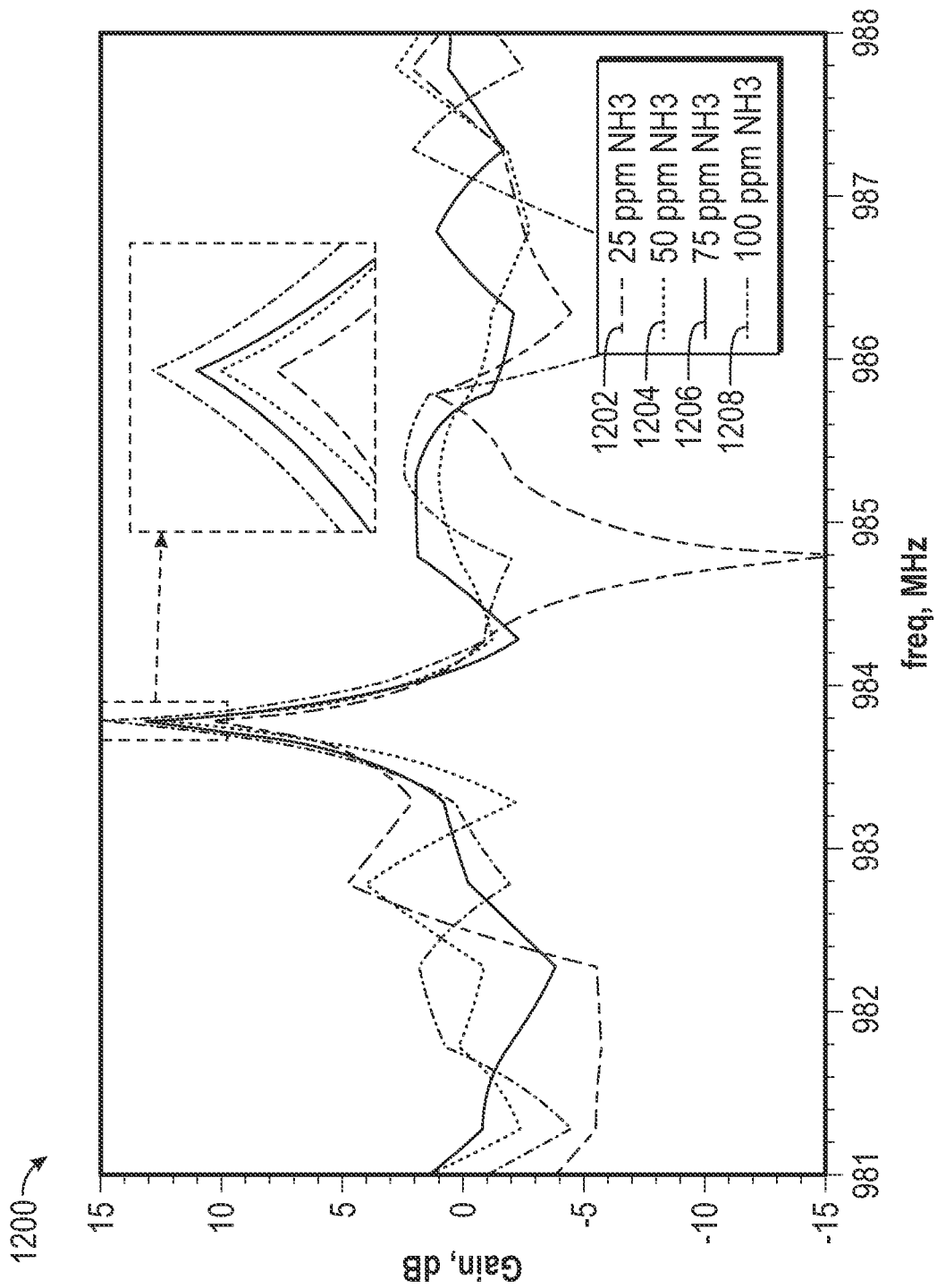
FIG. 12 illustrates a wireless gain profile as a function of transmitting frequency for an ammonia concentration between 25 ppm to 100 ppm, in accordance with an embodiment of the present disclosure.
Figure 13:
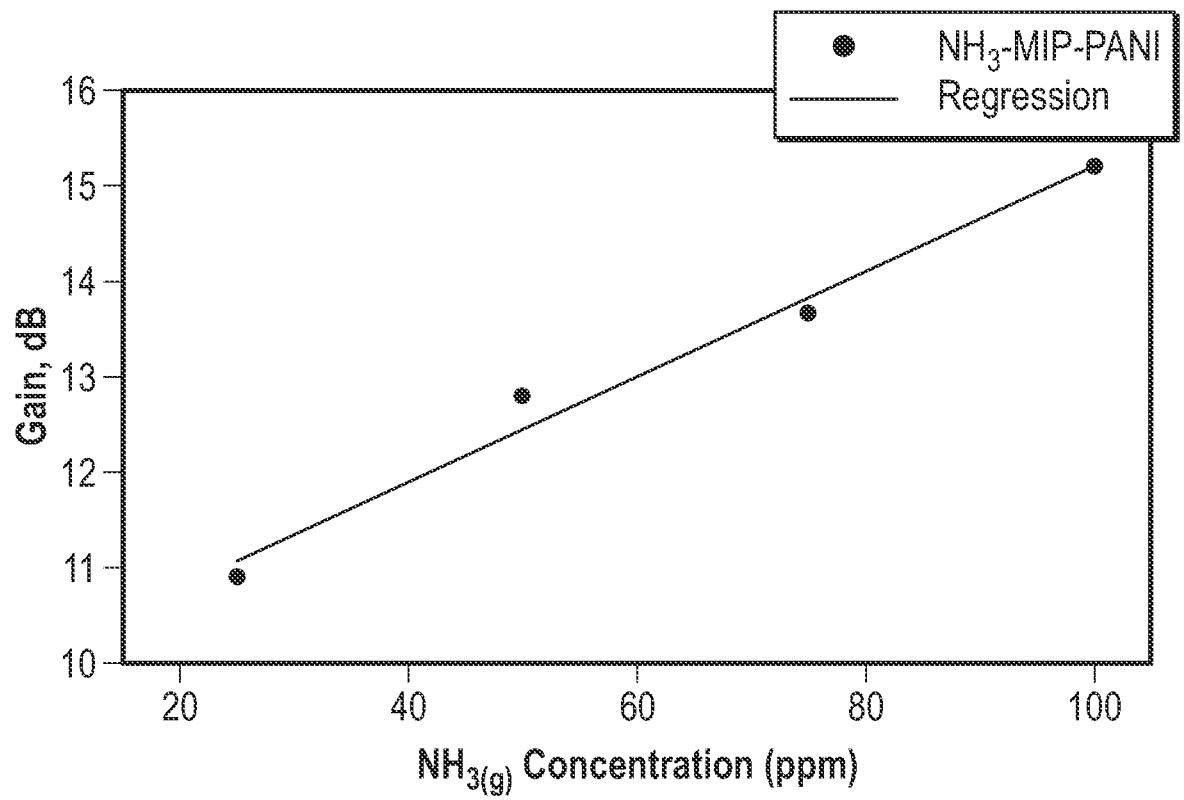
FIG. 13 illustrates an ammonia concentration calibration curve that can be based on wireless gain, in accordance with an embodiment of the present disclosure.

FIG. 12 illustrates a wireless gain profile as a function of transmitting frequency for an ammonia concentration between 25 parts-per-million (ppm) to 100 ppm. In an example, the wireless gain profile correlates with ammonia concentration. In an example, an ammonia concentration that can be detected in the VOC chamber is at least 25 ppm based on a flow meter being used. However, smaller concentrations can be detected with different flow meters that can adjust for lower ammonia flow rates and to investigate and detect smaller ammonia concentrations. In an example, the resonant frequency used was 983.7 Mhz with a high Q factor. In an example, a resonance peak can correlate with an ammonia concentration as shown in FIG. 12 at 1200. The resonance gain peak can be higher when an ammonia concentration is higher. Due to a high Q factor of about 8100, lower minimum detectable concentration can be achieved with the MIP sensor 104. The ammonia concentration calibration curve based on FIG. 12 is shown in FIG. 13 that has a linear relation where FIG. 13 illustrates an ammonia concentration calibration curve that can be based on wireless gain. This approach can be followed to optimize configurations of the MIP sensor 104.

As may be seen with reference to FIG. 12, at 25 ppm $NH_3$, readings correspond to the line 1202. At 50 ppm $NH_3$, readings correspond to the line 1204. At 75 ppm $NH_3$, readings correspond to the line 1206. At 100 ppm $NH_3$, readings correspond to the line 1208.

In examples, the MIP sensor 104 can be made of polyether synthetic paper, polyester synthetic paper, a polymeric substrate, a conductive polymer, and conductive silver ink. In addition, the MIP sensor 104 can be formed from cellulose, nitrocellulose, PVDF paper along with non-cellulosic material. Components of the MIP sensor 104 can be printed by an inkjet printer as noted above such that NIP sensor 104 can be integrated with the dipole antenna 200 via inkjet printing. The conductive polymer can be molecularly imprinted in order to hybridize with specific VOC molecules. The sensing signals from the MIP sensor 104 having back scattered RF signals can be screened. The MIP sensor 104 can be made with low cost paper with the dipole antenna 200, Moreover, the MIP sensor 104 can be a batteryless device.

The MIP sensor 104 can be a wireless sensor and can be deployed for long term batteryless, low cost large number deployments. The MIP sensor 104 can incorporate wireless sensing applications and can be used for VOC sensing, environmental monitoring, applications in the food industry, medical detection applications, and agricultural applications. For instance, applications in the food industry, such as food safety, require precise, low cost, and continuous detection of food spoilage in various environments, including refrigerator environments. The MIP sensor 104 can be used for such applications. Furthermore, the MIP sensor 104 can be used to monitor plant health level in agricultural applications in order to provide more precise agricultural output.

Advantages of the MIP sensor 104 can include the MIP sensor 104 being low cost, batteryless, and being printable as a "synthetic paper sensor" in order to detect physical, chemical, and biological conditions with considerably longer deployment time in a UHF communication range, such as a range up to about 1 GHz, Furthermore, the MIP sensor 104 allows for greater communication distances between the MIP sensor 104 and other devices, such as the network analyzer 110. For example, the communication distance can be greater than 30 cm. Moreover, the MIP sensor 104 enables new data analysis by sensing data in order to assist with decision making with respect to articles being monitored by the MIP sensor 104.

According to examples, a UWB based sensor is position sensitive that precisely aligns the transmission and receiving antenna. The configuration of a molecular imprinting structure with a dipole antenna as described herein can use circulatory polarized antennas that remove position sensitivity. This configuration can allow for obtaining sensing data reliably at long distances.

As a result of using a circularly polarized antenna and dipole antenna configuration, it is possible to detect sensing inside of the area 102, such as a polymer box or film, as shown in FIG. 1. Typically, UWB based paper sensors have difficulty detecting chemicals in polymer boxes due to issues associated with communicating with devices outside of the polymer box. RF communications can eliminate these problems.

In an example, the MIP sensor 104 disclosed herein is designed smaller than a UWB based paper sensor and has higher sensitivity when compared to UWB devices due to better communication. In addition, the MIP sensor 104 disclosed herein may operate at frequencies above 1.7 GHz.

Accordingly, the MIP sensor is smaller, allows for more reliable communications and for longer distance communications. Moreover, the MIP sensor has higher sensitivity that can be used for a greater variety of sensing applications. In addition, the MIP sensor can include porphyrin based sensing elements.

Figure 14:
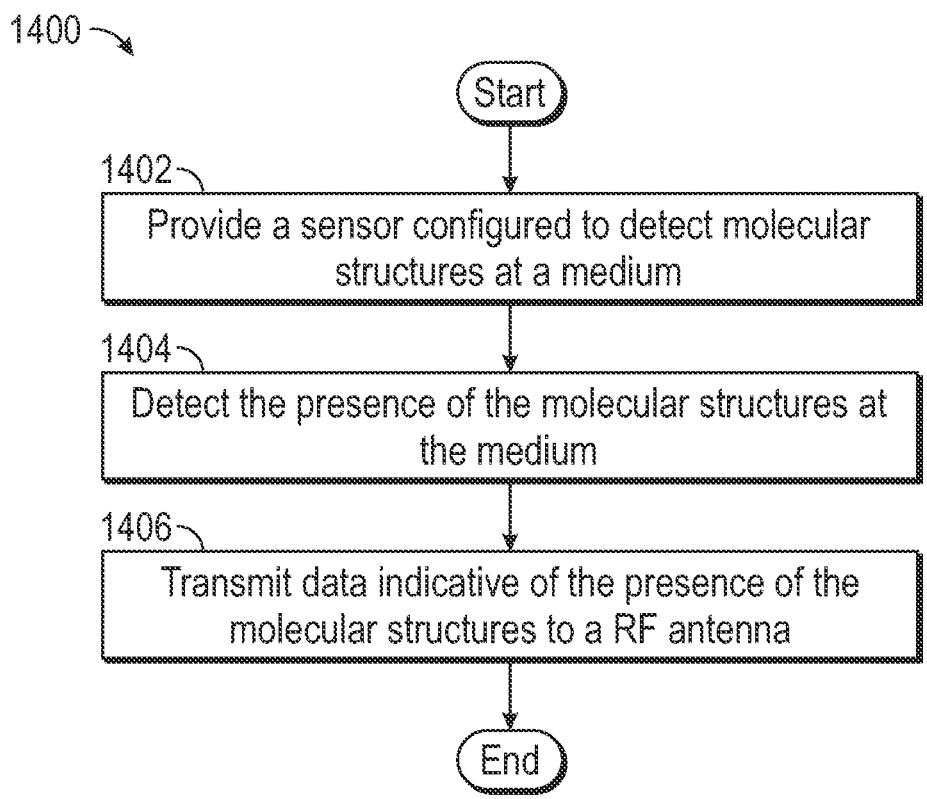
FIG. 14 shows a method for detecting the presence of molecular structures, in accordance with an embodiment of the present disclosure.

Now making reference to FIG. 14, a method 1400 for detecting the presence of molecular structures is disclosed. Initially, a sensor configured to detect molecular structures in a medium is provided during an operation 1402. For example, during the operation 1402, the MIP sensor 104 can provided at the area 102, which can function as a medium. In the example, the MIP sensor 104 includes the dipole antenna 200 along with the MIP conductive polymer sensing element 202. Moreover, in the example, the MIP sensor 104 is configured to detect the presence of the molecular structures 314, as discussed above.

After the operation 1402, the method 1400 can perform an operation 1404, where the sensor provided during the operation 1402 can detect the presence of the molecular structures at the medium. Returning to the example, after the MIP sensor 104 is placed at the area 102, the MIP sensor 104 can detect the presence of the molecular structures 314 during the operation 1404. As detailed above, the MIP conductive polymer sensor element 202 can capture the molecular structures 314. During the operation 1404, when the dipole antennas 200 are energized via the RF wireless antenna 106 as discussed above, the molecular structures 314 captured by the MIP conductive polymer sensor element 202 can be detected during the operation 1404 in accordance with the principles detailed herein.

Returning to the method 1400, after detection of the molecular structures during the operation 1404, the method 1400 performs an operation 1406, where data indicative of the presence of the molecular structures is transmitted to a RF wireless communication antenna. Referring back to the example, during the operation 1404, the dipole antenna 200 communicates the data gleaned from the Mil) conductive polymer sensor element 202 as discussed above to the RF wireless antenna 106 during the operation 1406. After completion of the operation 1406, the method 1400 is complete.

Figure 15:
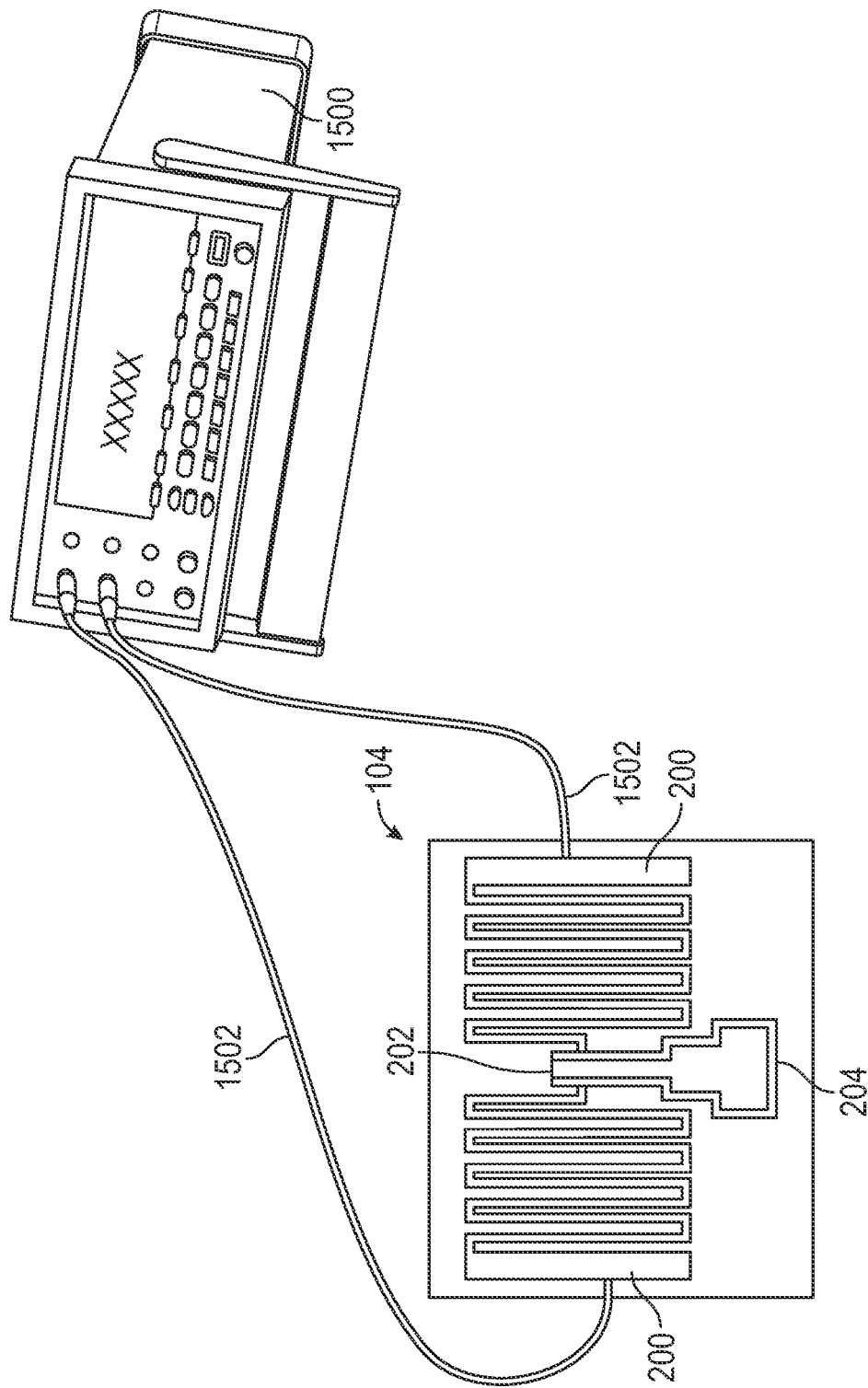
FIG. 15 illustrates a wired coupling between a MIP sensor and a multimeter, in accordance with an embodiment of the present disclosure.

In further examples, the MIP sensor 104 can have a wired configuration as shown with reference to FIG. 15. In an example, the MIP sensor 104 can have a wired connection with a multimeter 1500 via wiring 1502, as shown with reference to FIG. 15. In this example, the wiring 1502 operatively couples, such as through any suitable electrical connection, to each of the dipole antennae 200. During a sensing operation, the multimeter 1500 provides energization to the dipole antennae 200 via the wiring 1502. When the dipole antennae 200 are energized via the wiring 1502, a concentration of the molecular structures 314 captured by the MIP sensor 104 can be measured as discussed above. Moreover, data corresponding to the captured molecular structures 314, such as a concentration of the molecular structures 314, can be transmitted to the multimeter 1500 via the wiring 1502, where the multimeter 1500 can output a concentration determined as discussed herein. Therefore, the MIP sensor 104 can function as described above with reference to FIGS. 1-14 using the configuration shown in FIG. 15.

Although embodiments have been described with reference to specific example embodiments, it will be evident that various modifications and changes may be made to these embodiments without departing from the broader scope of the invention. Accordingly, the specification and drawings are to be regarded in an illustrative rather than a restrictive sense. The accompanying drawings that form a part hereof show by way of illustration, and not of limitation, specific embodiments in which the subject matter may be practiced. The embodiments illustrated are described in sufficient detail to enable those skilled in the art to practice the teachings disclosed herein. Other embodiments may be used and derived therefrom, such that structural and logical substitutions and changes may be made without departing from the scope of this disclosure. This description, therefore, is not to be taken in a limiting sense, and the scope of various embodiments is defined only by the appended claims, along with the full range of equivalents to which such claims are entitled.

What is claimed is:

1. A batteryless sensor comprising:
an ultra-high frequency (UHF) dipole antenna configured to transmit data to a radio frequency (RF) wireless communication antenna; and
a sensing element operatively coupled to the dipole antenna and disposed on a polymeric and cellulosic substrate, wherein the sensing element is configured to detect molecular structures.

2. The sensor of claim 1, wherein the dipole antenna receives power and transmits to the RF wireless communication antenna in a range up to 1.5 GHz.

3. The sensor of claim 1, wherein the sensing element includes a molecular imprinted conductive or non-conductive polymer sensing element and the sensing element is configured to detect one of organic and inorganic compounds, bio emanates, and biological compounds.

4. The sensor of claim 3, wherein the sensing element is configured to detect molecular structures in an aerosol.

5. The sensor of claim 1, wherein the sensor is configured to couple with a medium and detect a presence of the molecular structures in the medium and the molecular structure is one of a food product or medical diagnostics.

6. A system for detecting molecular structures, the system comprising:

a radio frequency (RF) wireless antenna;
a batteryless sensor, the sensor including:
an ultra-high frequency (UHF) dipole antenna configured to transmit data to the RF wireless antenna;
a sensing element operatively coupled to the dipole antenna and configured to detect molecular structures; and
a network analyzer configured to receive data from the RF wireless antenna.

7. The system of claim 6, wherein the sensing element is disposed on a polymeric and cellulosic substrate.

8. The system of claim 6, wherein the network analyzer is configured to determine an amount of the molecular structures detected by the sensing element.

9. The system of claim 6, wherein the dipole antenna receives power and transmits to the RF wireless antenna in a range up to 1.5 GHz.

10. The system of claim 6, wherein the sensing element includes a molecular imprinted conductive polymer sensing element and the sensing element detects organic and inorganic compounds.

11. The system of claim 6, wherein the sensor is configured to couple with a medium and detect a presence of the molecular structures in the medium and the medium is a food product.

12. The system of claim 11, wherein the network analyzer is configured to determine an amount of the molecular structures detected by the sensing element and emitted by the food product.

13. The system of claim 6, wherein the sensing element is configured to detect molecular structures in an aerosol.

14. A method for detecting a presence of molecular structures on a medium, the method comprising:
providing a sensor having a dipole antenna and a sensing element configured to detect the molecular structures at the medium;
detecting the presence of the molecular structures at the medium; and
transmitting, from the dipole antenna, data indicative of the presence of the molecular structures to a radio frequency (RF) wireless communication antenna.

15. The method of claim 14, wherein the medium is one of a food product, human body, or plant leaf.

16. The method of claim 14, wherein the sensing element is disposed on a polymeric, cellulosic substrate.

17. The method of claim 14, wherein the dipole antenna receives power and transmits to the RF wireless communication antenna in a range up to 1.5 GHz.

18. The method of claim 14, wherein the sensing element includes a molecular imprinted conductive or non-conductive polymer sensing element and the sensing element detects organic and inorganic compounds.

19. The method of claim 14, wherein the sensor is configured to couple with the medium and detect a presence of the molecular structures of the medium.

20. The method of claim 14, wherein the sensing element is configured to detect molecular structures in an aerosol.

* * * * *